United States Patent [19]

Fujioka et al.

[11] Patent Number: 4,601,835
[45] Date of Patent: Jul. 22, 1986

[54] HYDROXYALKOXY NORBORNYL ETHERS, PROCESS FOR PREPARING SAME AND ORGANOLEPTIC USES THEREOF

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[21] Appl. No.: 742,276

[22] Filed: Jun. 7, 1985

Related U.S. Application Data

[60] Division of Ser. No. 646,013, Aug. 31, 1984, which is a continuation-in-part of Ser. No. 574,150, Jan. 26, 1984, Pat. No. 4,521,634, which is a continuation-in-part of Ser. No. 533,915, Sep. 19, 1983, Pat. No. 4,532,364, which is a continuation-in-part of Ser. No. 507,292, Aug. 1, 1983, abandoned.

[51] Int. Cl.$^4$ .......................... A61K 7/46; C11B 9/00; C11D 3/50
[52] U.S. Cl. ................................ 252/8.9; 252/174.11; 252/522 R; 424/69
[58] Field of Search ............ 568/665; 252/8.9, 174.11, 252/522 R; 424/69

[56] References Cited

U.S. PATENT DOCUMENTS 4,393,247  7/1983  Sprecker ........................... 568/665

Primary Examiner—Dennis L. Albrecht
Attorney, Agent, or Firm—Arthur L. Liberman

[57] ABSTRACT

Described are the hydroxyalkoxy norbornyl ethers or mixtures of same having the structure:

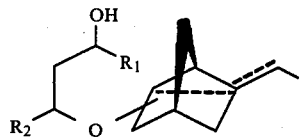

wherein one of $R_1$ or $R_2$ is methyl and the other of $R_1$ or $R_2$ is hydrogen and wherein one of the dashed lines represents a carbon-carbon bond and the other of the dashed lines represents no bond as well as methods for augmenting or enhancing the aroma of consumable materials including perfumes, colognes and perfumed articles by adding thereto an aroma augmenting or enhancing quantity of at least one of said hydroxyalkoxy norbornyl ethers.

5 Claims, 7 Drawing Figures

FIG.1
GLC PROFILE FOR EXAMPLE I.
CRUDE
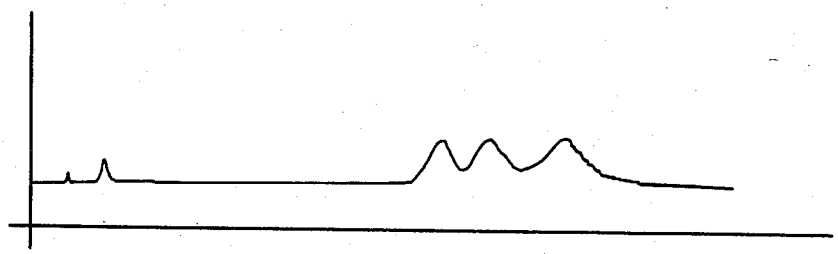
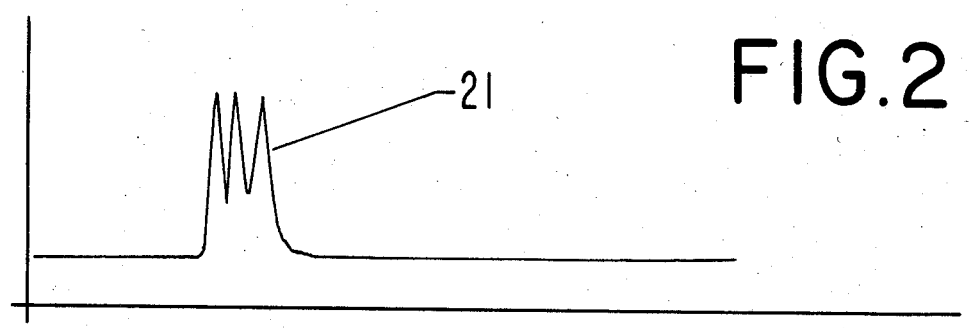
FIG.2
GLC PROFILE FOR EXAMPLE I,
FIRST DISTILLATION
FIG.3
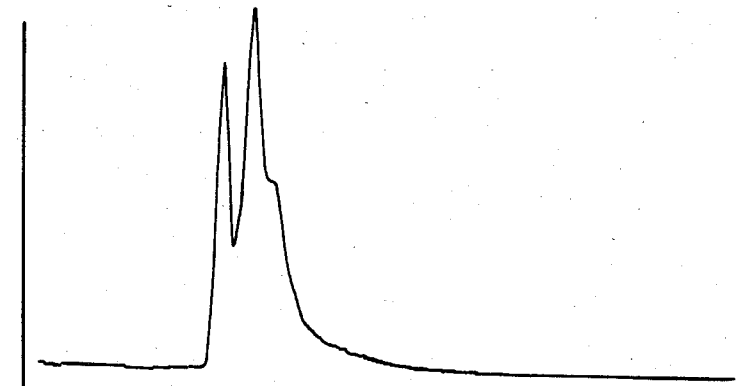
GLC PROFILE FOR BULKED FRACTIONS 4-11
SECOND DISTILLATION OF EXAMPLE I.

NMR SPECTRUM FOR PEAK 21 OF FIG. 2
EXAMPLE I

HYDROXYALKOXY NORBORNYL ETHERS, PROCESS FOR PREPARING SAME AND ORGANOLEPTIC USES THEREOF

This is a divisional of application Ser. No. 646,013, deposited in the U.S. Patent & Trademark Office on 8/31/84, which, in turn, is a continuation-in-part of application for U.S. Letters Patent, Ser. No. 574,150 filed on 1/26/84, now U.S. Pat. No. 4,521,634 issued on 6/4/85; which, in turn, is a continuation-in-part of application for U.S. Letters Patent, Ser. No. 533,915 filed on 9/19/83; now U.S. Pat. No. 4,532,364; which, in turn, is a continuation-in-part of application for U.S. Letters Patent, Ser. No. 507,292 filed on 8/1/83, now abandoned.

BACKGROUND OF THE INVENTION

The instant invention provides hydroxyalkoxy norbornyl ethers defined according to the structure:

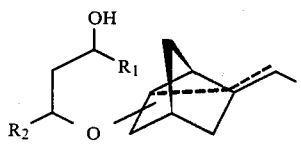

wherein one of $R_1$ or $R_2$ is methyl and the other of $R_1$ or $R_2$ is hydrogen and wherein one of the dashed lines represents a carbon-carbon bond and the other of the dashed lines represents no bond as well as the use thereof for augmenting or enhancing the aroma of perfume compositions, colognes and perfumed articles.

Inexpensive chemical compositions of matter which can provide fruity, green, herbaceous and floral aromas with anise-like, alliaceous and parsley-like topnotes are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

Hydroxyethoxy norbornane derivatives having the structures:

and

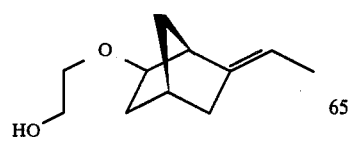

prepared according to the reaction:

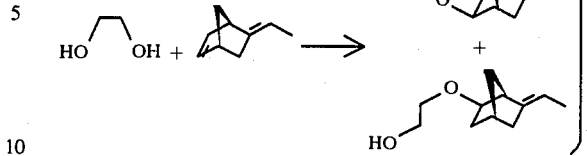

are disclosed as having green and raw potato aromas with galbanum topnotes in U.S. Pat. No. 4,393,247 issued on July 12, 1983 (the specification for which is incorporated by reference herein).

Furthermore, oxo reaction products have heretofore been produced for augmenting or enhancing the aroma of perfume compositions, perfumed articles and colognes. Thus, ether carboxaldehydes are well known in the art of perfumery for augmenting or enhancing the aroma of perfume compositions or perfumed articles. U.S. Pat. No. 4,359,390 issued on Nov. 16, 1982, the specification for which is incorporated by reference herein, discloses the use of such ether carboxaldehydes such as the compound having the structure:

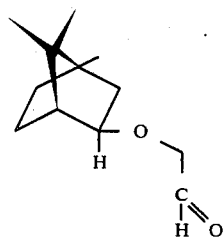

in augmenting or enhancing the aroma of perfume compositions, colognes and perfumed articles. Application for United States Letters Patent, Ser. No. 335,794 filed on Sept. 26, 1983, the specification for which is incorporated by reference herein, discloses 5-alkoxy-bicyclo[2.2.1]heptane-2-oxypropane derivatives. The invention of Ser. No. 335,794 relates to 5-alkoxy-bicyclo[2.2.1]heptane-2-oxypropane derivatives defined according to the structure:

(wherein R represents $C_1$-$C_3$ alkyl and wherein Z represents one of the moieties, carbinol having the structure:

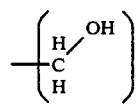

or carboxaldehyde having the structure:

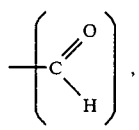

and uses thereof in augmenting or enhancing the aroma of perfume compositions, colognes or perfumed articles (e.g., solid or liquid anionic, cationic, nonionic or zwitterionic detergents, fabric softener compositions, fabric softener articles, cosmetic powders, hair preparations, perfumed polymers and the like).

Nothing in the prior art, however, suggests either implicitly or explicitly the unexpected, unobvious and advantageous properties of the hydroxyalkoxy norbornyl ethers of our invention defined according to the structure:

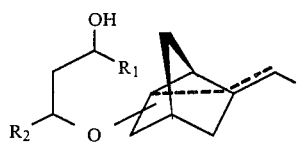

wherein one of $R_1$ or $R_2$ is methyl and the other of $R_1$ or $R_2$ is hydrogen and wherein one of the dashed lines represents a carbon-carbon bond and the other of the dashed lines represents no bond.

BRIEF DESCRIPTION OF THE DRAWINGS

FIG. 1 is the GLC profile for the crude reaction product of Example I containing a mixture of compounds having the structures:

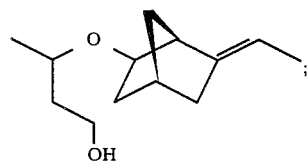

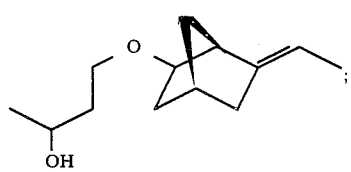

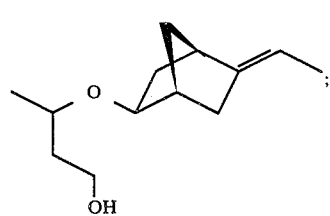

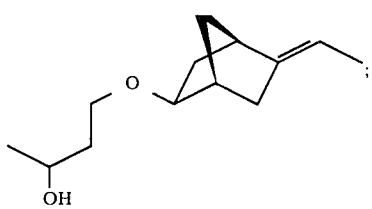

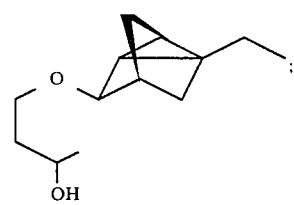

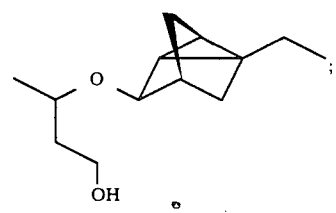

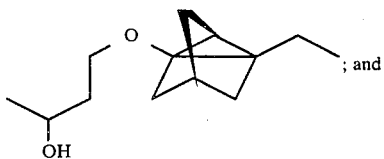

; and

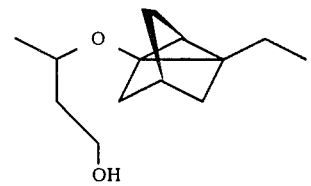

FIG. 2 is the GLC profile for the first distillation product of the reaction product of Example I containing the compounds having the structures:

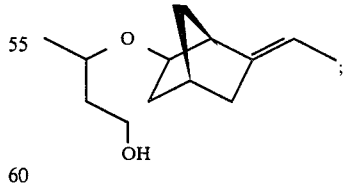

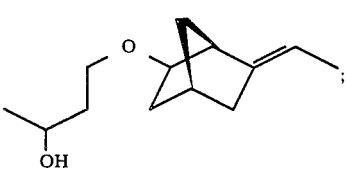

Figure 4:
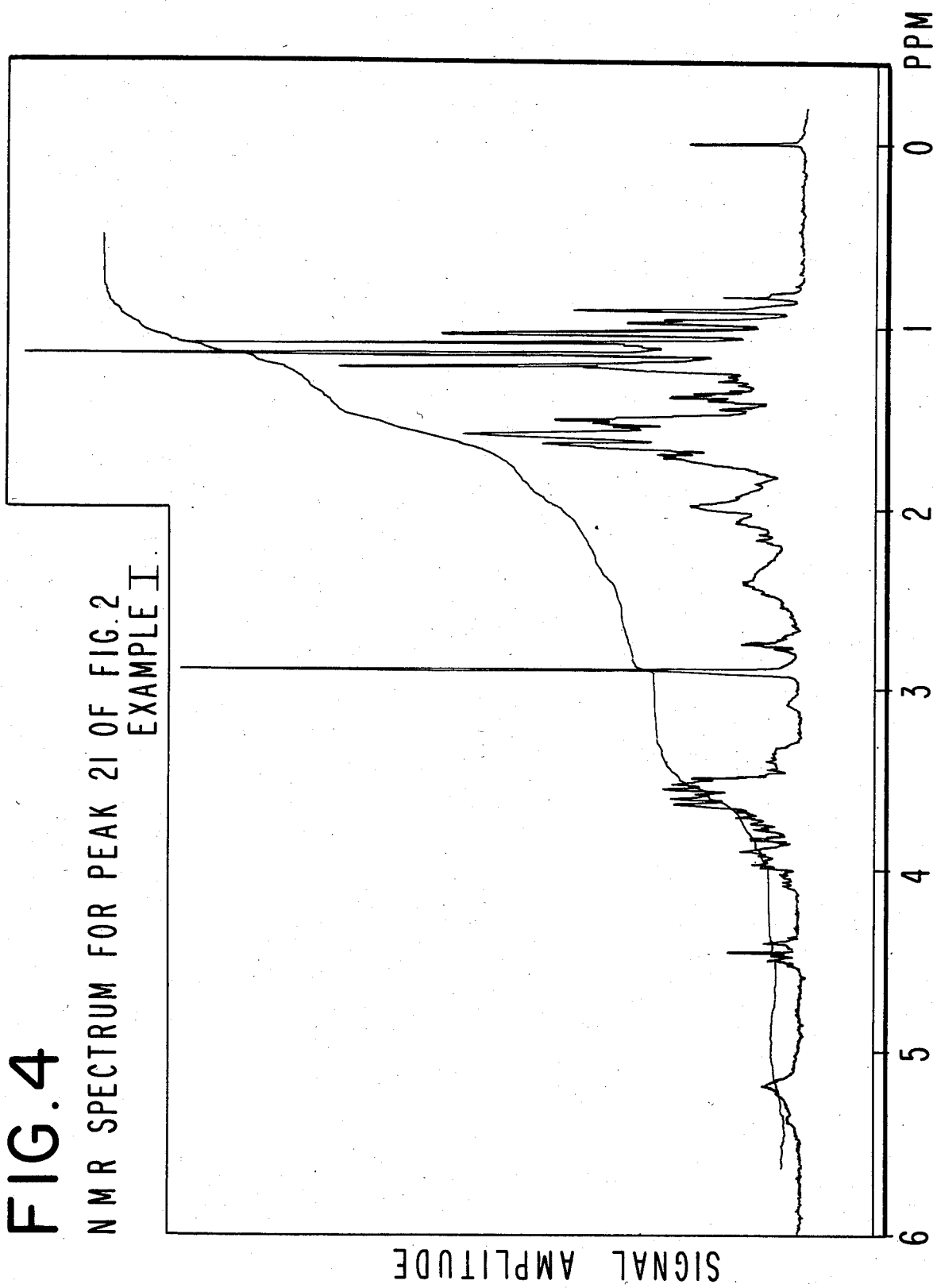
Figure 5:
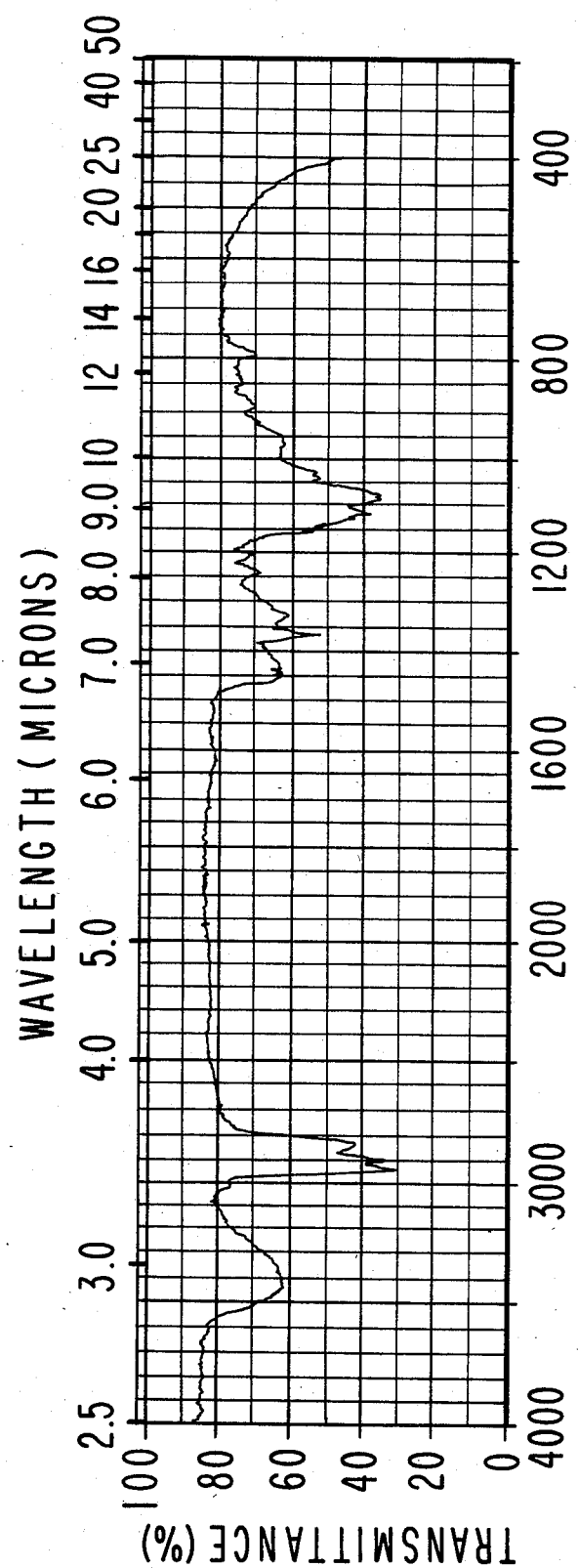

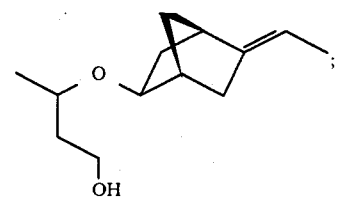
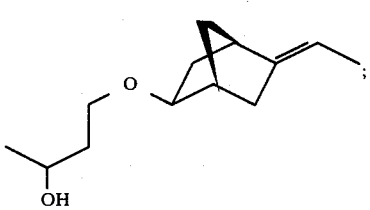
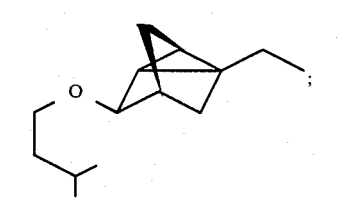
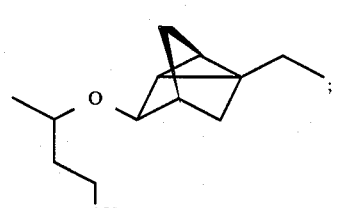
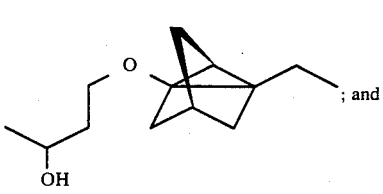
; and
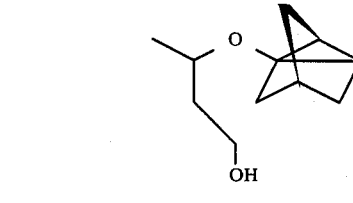
.
FIG. 3 is the GLC profile for bulked fractions 4–11 of the second distillation of the reaction product of Example I containing the compounds having the structures:
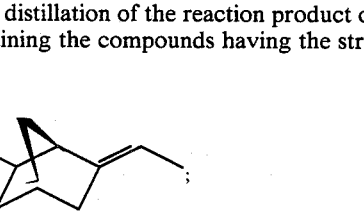
;
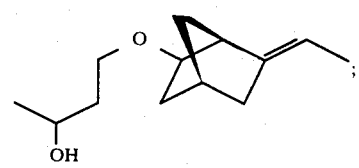
;
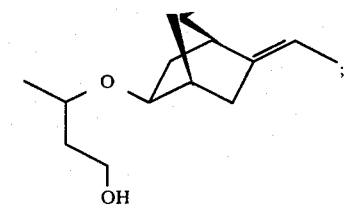
;
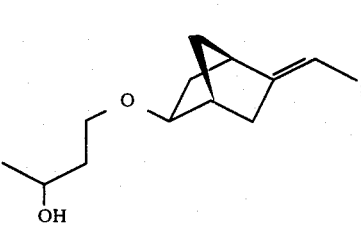
;
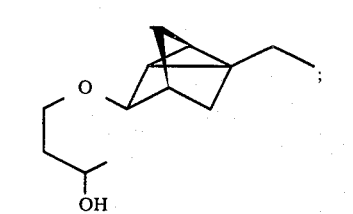
;
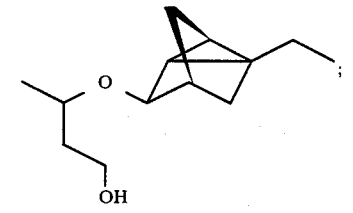
;
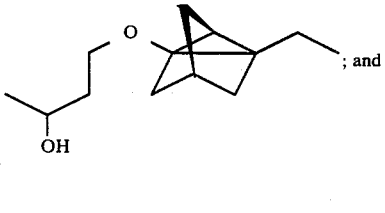
; and
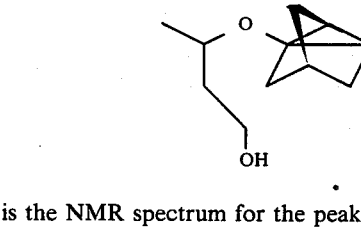
.
FIG. 4 is the NMR spectrum for the peak indicated by Reference Numeral 21 on FIG. 2 and is for the mixture of compounds having the structures:

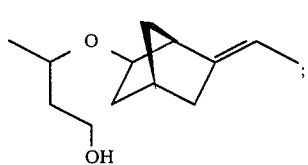
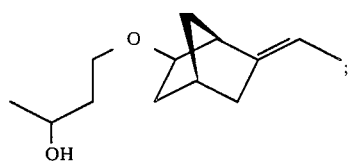
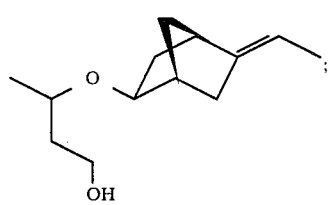
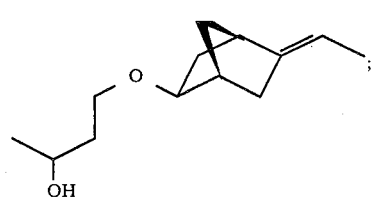
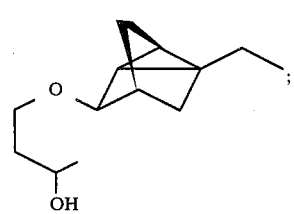
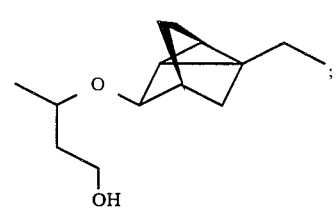
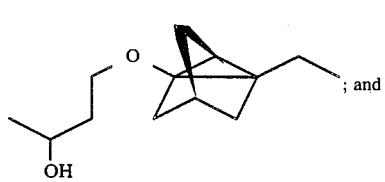
; and
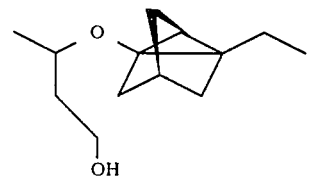
produced according to Example I.
FIG. 5 is the infra-red spectrum for the mixture of compounds having the structures:
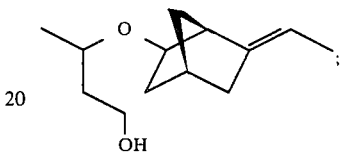
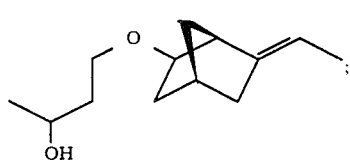
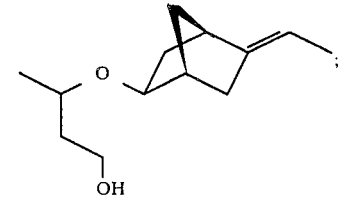
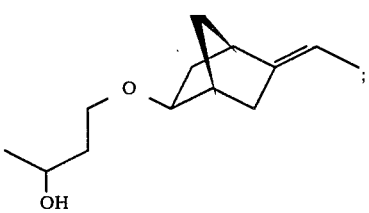
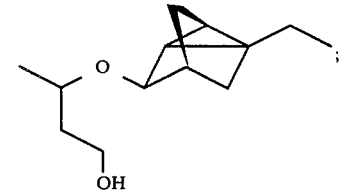

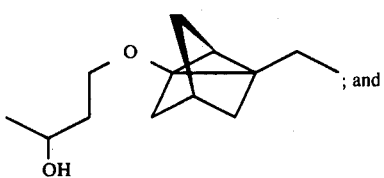; and

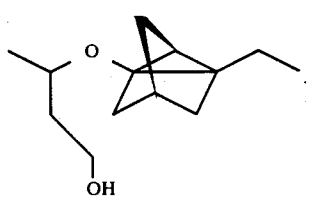

produced according to Example I (the peak indicated by Reference Numeral 21 of the GLC profile of FIG. 2).

Figures 6, 7:
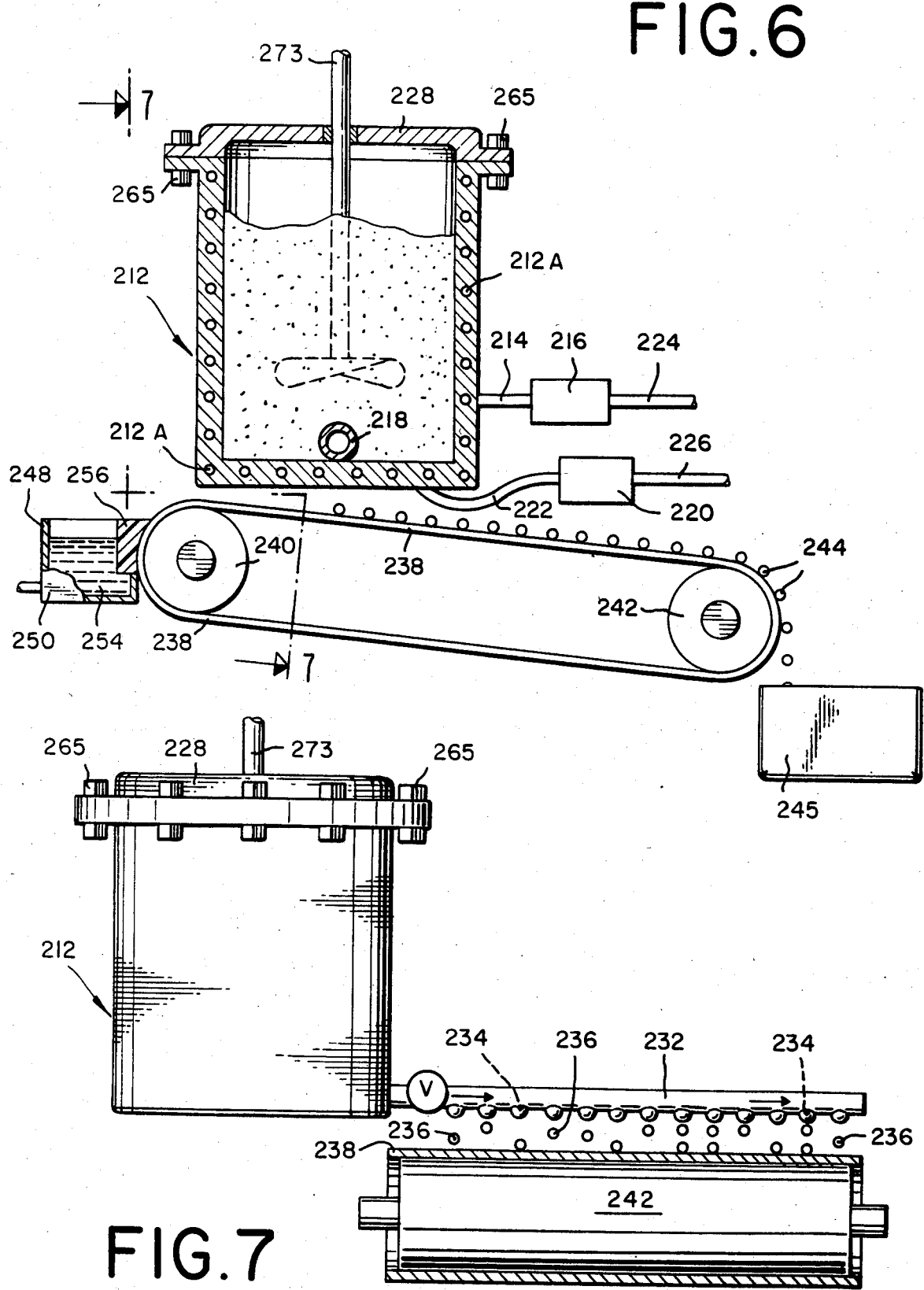

FIG. 6 represents a cutaway side elevation view of the apparatus used in forming perfumed polymers which contain embedded therein at least one of the hydroxyalkoxy norbornyl ethers of our invention defined according to the structure:

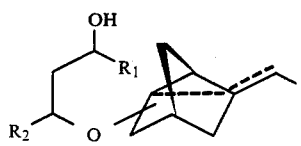

wherein one of $R_1$ or $R_2$ is methyl and the other of $R_1$ or $R_2$ is hydrogen and wherein one of the dashed lines represents a carbon-carbon bond and the other of the dashed lines represents no bond.

FIG. 7 is a front view of the apparatus of FIG. 6 looking in the direction of the arrows.

DETAILED DESCRIPTION OF THE DRAWINGS

FIG. 2 is the GLC profile for the first distillation of the reaction product of Example II containing the compounds having the structures:

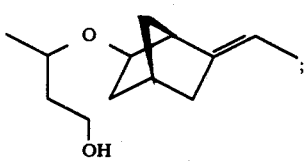;

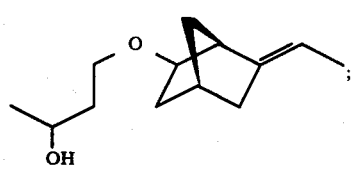;

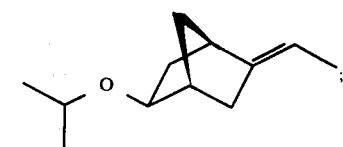;

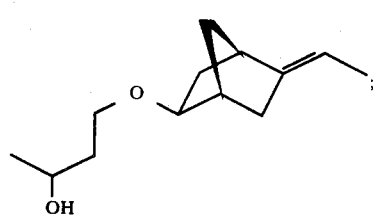;

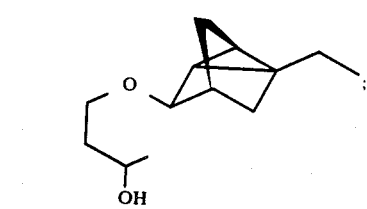;

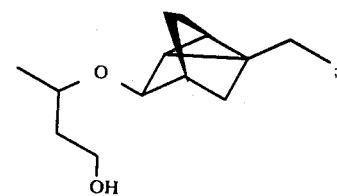;

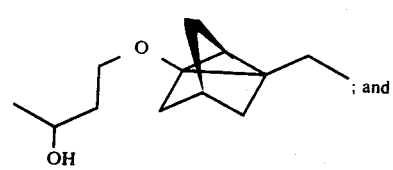;

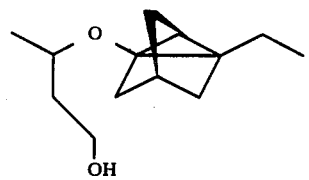

(Conditions: 6'×0.25" 10% SE-30 column programmed at 200° C., isothermal).

The peak indicated by Reference Numeral 21 is the peak for the mixture of compounds having the structures:

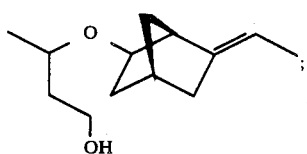

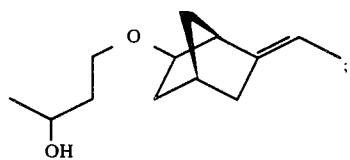

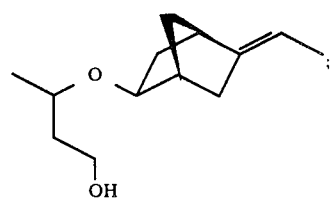

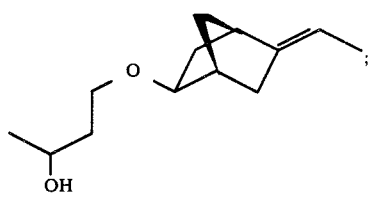

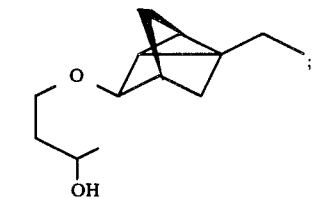

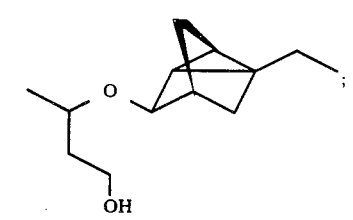

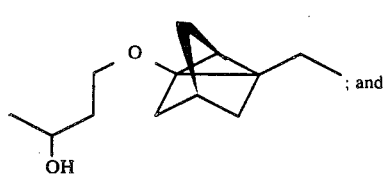; and

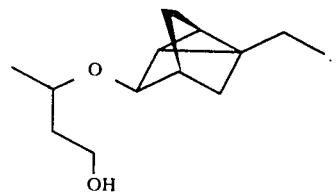

Referring to FIGS. 6 and 7, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 6 and 7, in particular, the apparatus used in producing such elements comprises a device for forming the polymer containing perfume, e.g., polyethylene or polyethylene-polyvinyl acetate or mixtures of same or polypropylene containing at least one of the hydroxyalkoxy norbornyl ethers of our invention taken alone or taken together with one or more additional perfume materials which comprises a vat or container 212 into which the polymer taken alone or in admixture with other copolymers and the perfuming substance which is at least one of the hydroxyalkoxy norbornyl ethers of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 Saybolt seconds. The heater 218 is maintained to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains at least one of the hydroxyalkoxy norbornyl ethers or our invention and, if desired, one or more of the perfume materials is quickly added to the melt. Generally, about 10–45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The control 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer is in intimate admixture with at least one of the hydroxyalkoxy norbornyl ethers of our invention taken alone or taken further together with one or more other perfume substances and in such admixture will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains at least one of the hydroxyalkoxy norbornyl ethers of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides hydroxyalkoxy norbornyl ethers defined according to the structure:

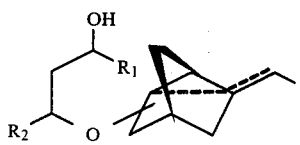

wherein one of $R_1$ or $R_2$ is methyl and the other of $R_1$ or $R_2$ is hydrogen and wherein one of the dashed lines represents a carbon-carbon bond and the other of the dashed lines represents no bond including compounds having the structures:

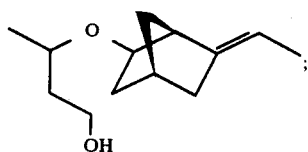

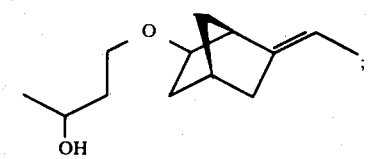

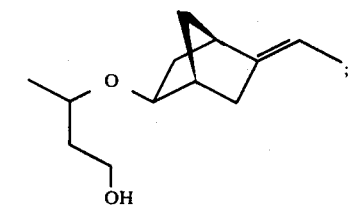

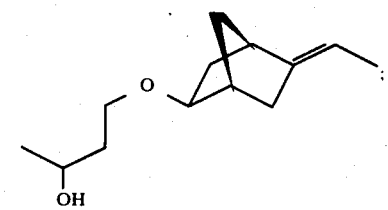

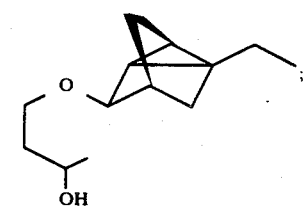

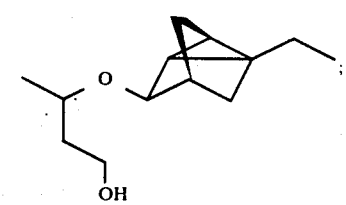

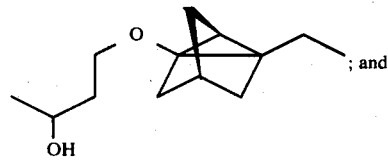

The present invention also provides a process for preparing the hydroxyalkoxy norbornyl ethers by means of reacting the compound having the structure:

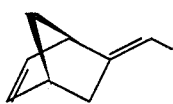

(ethylidene and norbornene) with 1,3-dihydroxy butane having the structure:

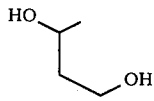

according to the reaction:

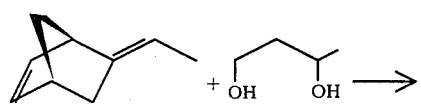

wherein one of $R_1$ or $R_2$ is methyl and the other of $R_1$ or $R_2$ is hydrogen and wherein one of the dashed lines represents a carbon-carbon bond and the other of the dashed lines represents no bond. More specifically this reaction can be so shown thusly:

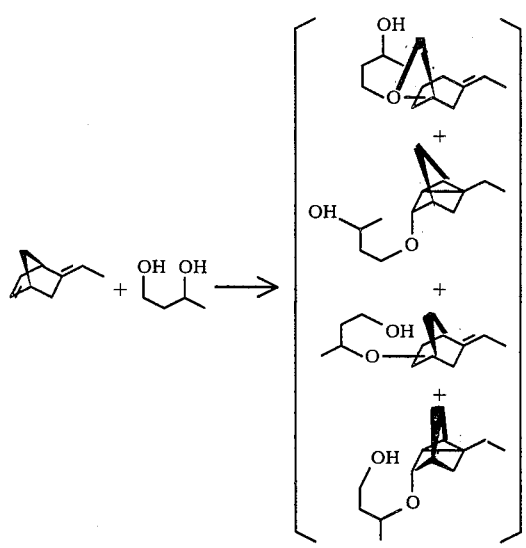

The present invention also provides a process for augmenting or enhancing the aroma of perfume compositions, colognes or perfumed articles by adding to such perfume compostion, cologne or perfumed article at least one of the hydroxyalkoxy norbornyl ethers of our invention having the structure:

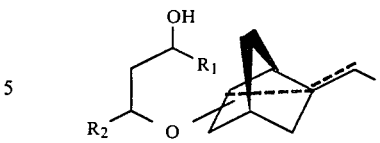

wherein one of $R_1$ or $R_2$ is methyl and the other of $R_1$ or $R_2$ is hydrogen and wherein one of the dashed lines represents a carbon-carbon bond and the other of the dashed lines represents no bond. The perfumed articles of our invention include soaps, anionic, cationic, nonionic and zwitterionic detergents, fabric softener compositions, fabric softener articles, optical brightener compositions, perfumed polymers, hair preparations and the like. Accordingly, a need in the field of perfumery as well as in the field of perfumed articles and cosmetics manufacture, is fulfilled by augmenting or enhancing the specific aromas in such perfume compositions, colognes and perfumed articles, e.g., fruity, green, herbaceous and floral aromas with anise-like, alliaceous and parsley-like topnotes.

The hydroxyalkoxy norbornyl ethers of our invention defined according to the structure:

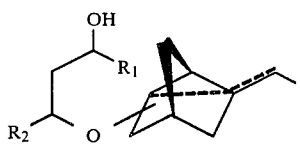

wherein one of $R_1$ or $R_2$ is methyl and the other of $R_1$ or $R_2$ is hydrogen and wherein one of the dashed lines represents a carbon-carbon bond and the other of the dashed lines represents no bond are prepared by reacting ethylidene norbornene having the structure:

with 1,3-butanediol having the structure:

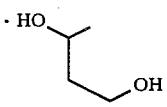

in the presence of a catalyst which is either a mineral acid or a Lewis acid. Examples of mineral acid catalysts are sulfuric acid, phosphoric acid, para-toluene sulfonic acid, methane sulfonic acid and acid ion-exchange resin. Examples of Lewis acid which can be used as catalysts are boron trifluoride etherate, aluminum chloride, zinc chloride, stannic chloride, stannous chloride, zinc bromide, diethyl aluminum chloride, ethyl aluminum dichloride, ethyl aluminum dibromide and diethyl aluminum bromide.

The reaction preferably takes place in the presence of an inert solvent such as tetrahydrofuran, toluene or benzene. The reaction may take place in the absence of the inert solvent and in the presence of an excess of the alcohol reactant, the excess of the alcohol reactant being used as the "solvent".

The reaction temperature may vary from about 25° C. up to about 120° C. with reflux temperature being preferred. The reflux temperature depends upon the pressure in the reactor and the particular solvent being used as well as its concentration. The mole ratio of acid catalyst to ethylidene norbornene may vary from about 1:99 up to about 1:10. The mole ratio of ethylidene norbornene reactant to alcohol reactant may vary from about 1:1 up to about 1:2 with a mole ratio of 1:1.5 of norbornene:alcohol reactant being preferred. Thus, the reaction to produce the compounds of our invention may be shown thusly:

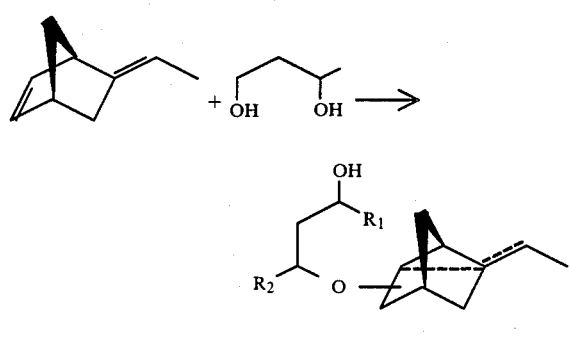

or thusly:

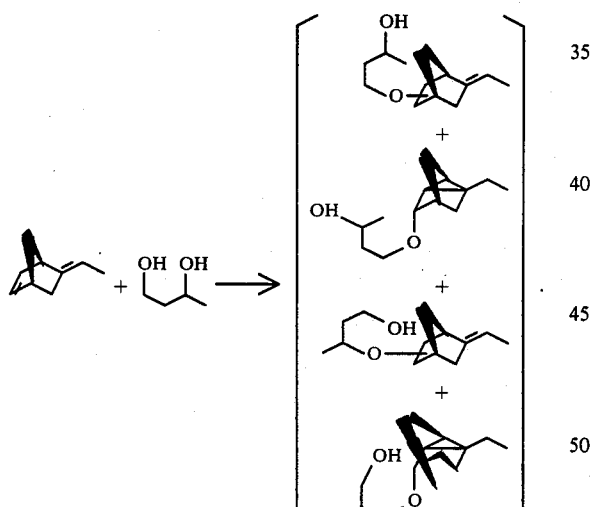

The compounds of our invention are prepared in admixture usually with these compounds in admixture having the structures:

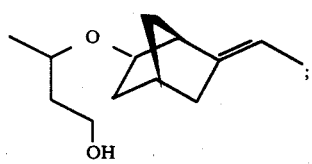

-continued

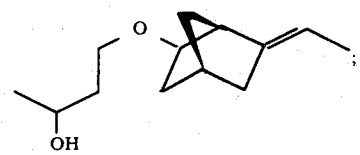

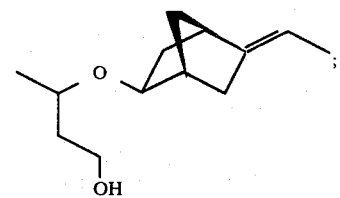

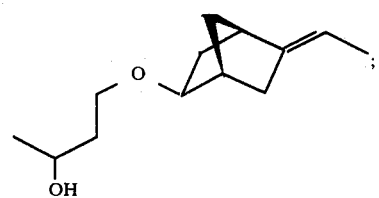

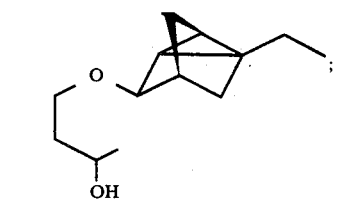

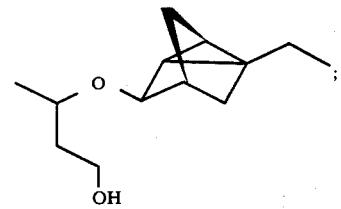

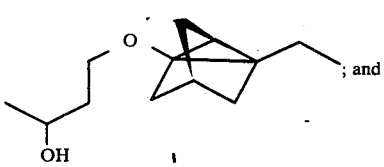

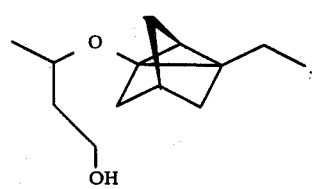

These compounds, however, may be separated by distillation, extraction and preparative GLC techniques in order to yield separately the compound having the structure:

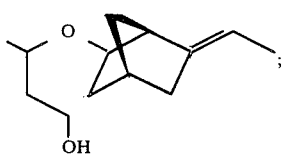

the compound having the structure:

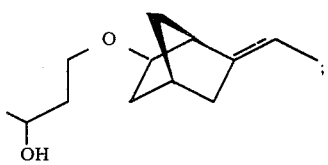

the compound having the structure:

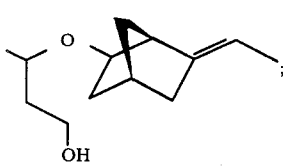

the compound having the structure:

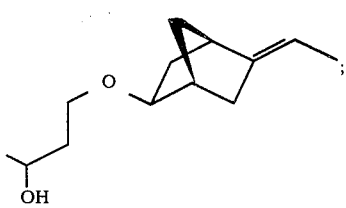

the compound having the structure:

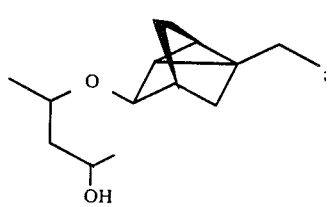

the compound having the structure:

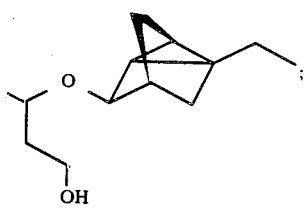

the compound having the structure:

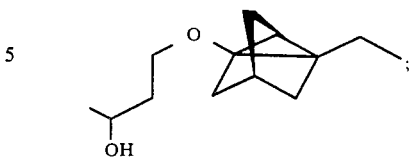

and the compound having the structure:

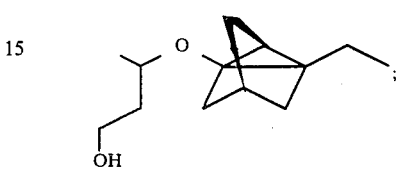

In addition, the compounds having the generic structure:

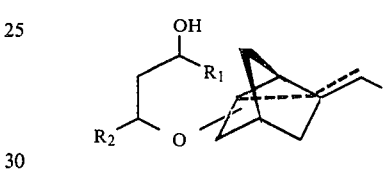

wherein one of $R_1$ or $R_2$ is methyl and the other of $R_1$ or $R_2$ is hydrogen and wherein one of the dashed lines represents a carbon-carbon bond and the other of the dashed lines represents no bond exist in isomeric forms and are produced in admixture. The mixture of these "endo" and "exo" and "cis" and "trans" isomers may be separated from one another by means of standard separation techniques including preparative GLC techniques whereby the individual isomers may be separated and then utilized individually. Structures of these isomers are as follows:

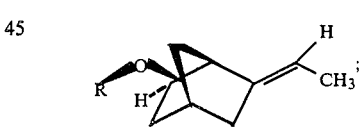

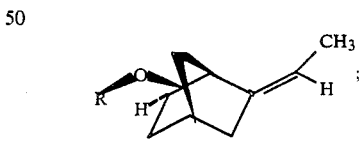

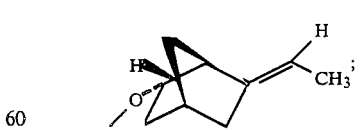

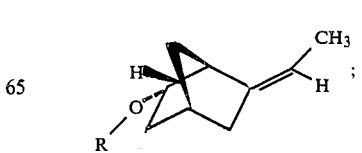

-continued

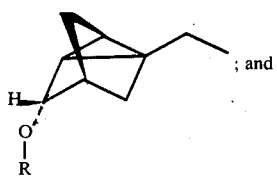

; and

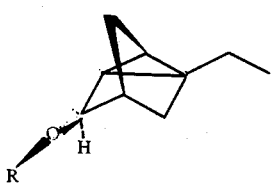

wherein R represents either:
(i) 3-methyl-3-hydroxypropyl; or
(ii) 1-methyl-3-hydroxypropyl.

At least one of the hydroxyalkoxy norbornyl ethers defined according to the structure:

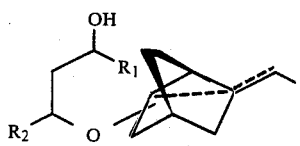

wherein one of $R_1$ or $R_2$ is methyl and the other of $R_1$ or $R_2$ is hydrogen and wherein one of the dashed lines represents a carbon-carbon bond and the other of the dashed lines represents no bond prepared in accordance with the process of our invention and one or more auxiliary perfume ingredients including, for example, alcohols other than the hydroxyalkoxy norbornyl ethers of our invention, ketones, aldehydes, terpinic hydrocarbons, nitriles, esters, lactones, natural essential oils and synthetic essential oils may be admixed so that the combined odors of the individual components produce a pleasant and desired fragrance, particularly and preferably in the fruity, green, herbaceous and floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, at least one of the hydroxyalkoxy norbornyl ethers of our invention defined according to the structure:

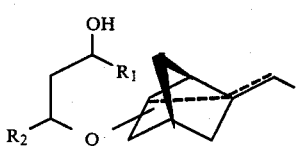

wherein one of $R_1$ or $R_2$ is methyl and the other of $R_1$ or $R_2$ is hydrogen and wherein one of the dashed lines represents a carbon-carbon bond and the other of the dashed lines represents no bond prepared in accordance with the process of our invention can be used to alter, modify or enhance the aroma characteristics of a perfume composition, for example, by utilizing or moderating the olfactory reaction contributed by another ingredient in the composition.

The amount of at least one of the hydroxyalkoxy norbornyl ethers of our invention prepared in accordance with the process of our invention, which will be effective in perfume compositions as well as perfumed articles (e.g., anionic, cationic, nonionic or zwitterioninc detergents, soaps, fabric softener compositions, drier-added fabric softener articles, optical brightener compositions, perfumed polymers, textile sizing agents and the like) and colognes depends on many factors, including the other ingredients, their amounts and the effects which are desired. It has been found that perfume compositions containing as little as 0.01% of one or more of the hydroxyalkoxy norbornyl ethers of our invention, or even less (e.g., 0.005%) can be used to impart, augment or enhance fruity, green, herbaceous and floral aromas with anise-like, alliaceous and parsley-like topnotes in or to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

At least one of the hydroxyalkoxy norbornyl ethers of our invention having the structure:

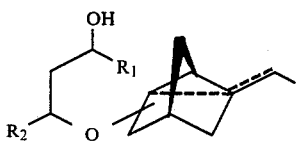

·wherein one of $R_1$ or $R_2$ is methyl and the other of $R_1$ or $R_2$ is hydrogen and wherein one of the dashed lines represents a carbon-carbon bond and the other of the dashed lines represents no bond is useful (taken alone or taken further together with other ingredients in perfume compositions) as (an) olfactory component(s) in detergents and soaps, space odorants and deodorants, perfumes, colognes, toilet water, bath preparations such as creams, deodorants, hand lotions and sun screens; powder, such as talcs, dusting powders, face powders and perfumed polymers and articles of manufacture produced from said perfumed polymers, e.g., garbage bags, children's toys and the like. When used as an olfactory component in perfumed articles, as little as 0.2% of at least one of the hydroxyalkoxy norbornyl ethers of our invention prepared in accordance with the process of our invention will suffice to impart, augment or enhance fruity, green, herbaceous and floral aromas with anise-like, alliaceous and parsley-like topnotes. Generally, no more than 6% of at least one of the hydroxyalkoxy norbornyl ethers of our invention based on the ultimate end product is required in the perfumed article. Accordingly, the range of at least one of the hydroxyalkoxy norbornyl ethers in the perfumed article is from about 0.2% by weight of the hydroxyalkoxy norbornyl ethers up to about 6% by weight of the hydroxyalkoxy norbornyl ethers based on the total weight of the perfumed article.

In addition, the perfumed composition or fragrance composition of our invention can contain a vehicle or carrier for at least one of the hydroxyalkoxy norbornyl ethers of our invention. The vehicle can be a liquid such as a non-toxic alcohol, e.g., ethyl alcohol, a non-toxic glycol, e.g., propylene glycol or the like. The carrier can be also an absorbent solid, such as a gum (e.g., gum arabic, guar gum, xanthan gum or the like) or components for encapsulating the composition (such as, for example, gelatin as by coacervation or such as a urea formaldehyde prepolymer which on polymerization forms a capsule shell around the liquid perfume center).

Our invention also relates to the utilization of controlled release technology for the controlled release of perfumes into gaseous environments from polymers such as mixtures of epsilon polycaprolactone polymer and polyethylene which polyepsilon caprolactone polymers are defined according to at least one of the structures:

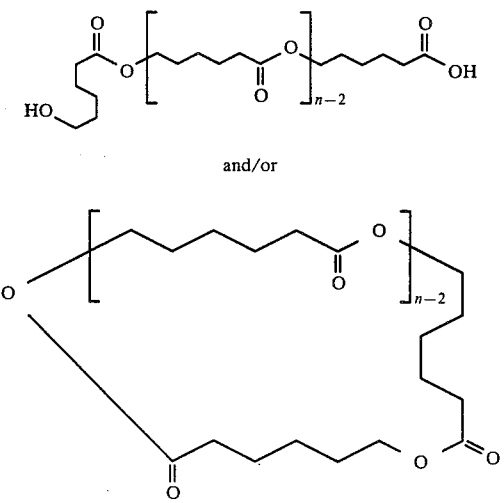

and/or wherein "n" is from about 50 up to about 1,200 with the proviso that the average "n" in the system varies from about 150 up to about 700 according to the mathematical statement:

$$[700 \geq \bar{n} \geq 150]$$

with the term $$\bar{n}$$

being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$[(dM_t)/(dt)] = k_1 e^{-k_2 t}$$

wherein $k_1$ and $k_2$ are constants. According to Kydonieus, "Controlled Release Technologies: Methods, Theory, and Applications" (cited, supra) the amount of perfume composition released is proportional to time as long as the concentration of perfume material present, e.g., at least one of the hydroxyalkoxy norbornyl ethers of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing at least one of the hydroxyalkoxy norbornyl ethers of our invention.

The polyepsilon caprolactone polymers useful in practicing our invention are more specifically described in the brochure of the Union Carbide Corporation, 270 Park Avenue, New York, N.Y., 10017, entitled "NEW POLYCAPROLACTONE THERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilized the polyepsilon caprolactone useful in conjunction with our invention against discoloration are dihydroxybenzenes such hydroquinone or compounds having the formula:

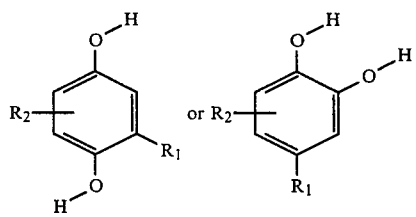

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or absorbed into the polymeric matrix.

The method of incorporating at least one of the hydroxyalkoxy norbornyl ethers of our invention or perfume compositions containing same into the polymers may be according to the techniques of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene-polyepsilon caprolactone polymer mixture (50:50) is mixed with at least one of the hydroxyalkoxy norbornyl ethers of our invention. Drops are formed from the mixture and the drops are then melted, if desired, with a second amount of unscented low density polyethylene, for example, or polypropylene, for example. Usually, but not necessarily, the second amount of polymer is larger than the first amount. The resulting mixture thus obtained, is solidified subsequent to or prior to ultimate casting into a utilitarian shape.

Thus, in accordance with one aspect of our invention, the imparting of scent is effected in two stages. In a first stage a 50:50 (weight:weight) polyepsilon caprolactone, e.g., PCL-700:polyethylene in molten form is admixed with a high percentage of at least one of the hydroxyalkoxy norbornyl ethers of our invention and the mixture is solidified in the form of pellets or beads. These pellets or beads thus contain a high percentage of at least one of the hydroxyalkoxy norbornyl ethers (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention, at least one of the hydroxyalkoxy norbonyl ethers of our invention is added to the polymer in a large closed container or drum which is maintained under controlled temperature conditions while the polymer in a melted condition is mixed with at least one of the hydroxyalkoxy norbonyl ethers under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the hydroxyalkoxy norbornyl ethers of our invention is permitted to drip through the orifices onto a continuously moving, cooled conveyor upon which the polymer containing at least one of the hydroxyalkoxy norbornyl ethers of our invention solidifies into small size pellets with the perfume imprisoned therein. The apparatus useful in conjunction with this process, advantageously includes a conveyor of a material which will not adhere to the polymer which contains at least one of the hydroxyalkoxy norbornyl ethers of our invention.

In order that the droplets form into uniform pellets or beads, the conveyor is continuously washed with a liquid, such as water to maintain the surface relatively cool. The pellets are delivered by the conveyor into a container and packaged for shipment.

The following Example I illustrates a process for preparing a mixture of compounds defined according to the structure:

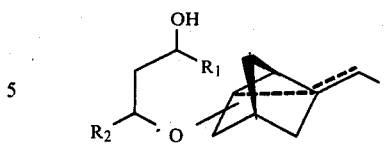

wherein one of $R_1$ or $R_2$ is methyl and the other of $R_1$ or $R_2$ is hydrogen and wherein one of the dashed lines represents a carbon-carbon bond and the other of the dashed lines represents no bond. Examples following Example I are illustrative of the organoleptic utilities of the hydroxyalkoxy norbornyl ethers of our invention. All parts and percentages given herein are by weight unless otherwise specified.

EXAMPLE I

PREPARATION OF 5-ETHYLIDENE-2-NORBORNENE ADDUCT OF 1,3-BUTANEDIOL

Reaction

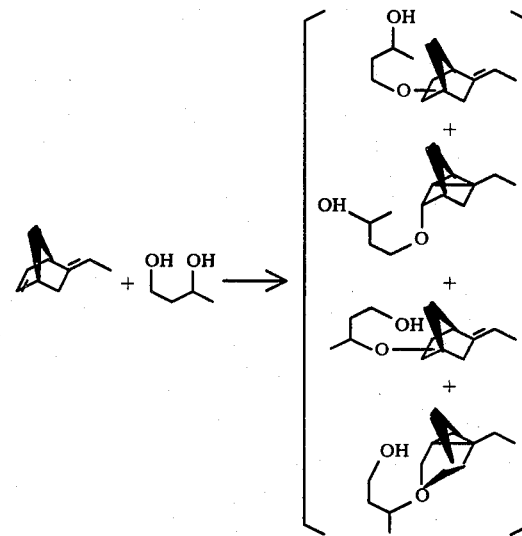

Into a 2 liter flask equipped with stirrer, condenser, thermometer and heating mantle is placed 500 grams (5.55 moles) of 1,3-butanediol. To the 1,3-butanediol is added 19 grams (0.13 moles) of boron trifluoride etherate. The mixture is then heated to 80° C. with stirring. 533.7 Grams (4.44 moles) of 5-ethylidene-2-norbornene is added over a 65 minute period while maintaining the reaction mass at 80° C. The reaction is complete after 70 minutes. 500 ml. Water is added to the hot reaction mass and the organic phase is separated from the aqueous phase. The organic phase is washed with one 1 liter portion of water followed by one 200 ml. portion of 10% aqueous sodium hydroxide followed by one 1.5 liter portion of aqueous saturated sodium chloride.

The reaction mass is then distilled on a 6" silver mirror splash column yielding the following fractions:

| FRACTION NO. | VAPOR TEMP. (°C.) | LIQUID TEMP. (°C.) | VACUUM mm/Hg. | WEIGHT OF FRACTION (gms) |
| --- | --- | --- | --- | --- |
| 1 | 23/103 | 114/123 | 3.4/3.0 | 10 |

-continued

| FRACTION NO. | VAPOR TEMP. (°C.) | LIQUID TEMP. (°C.) | VACUUM mm/Hg. | WEIGHT OF FRACTION (gms) |
|---|---|---|---|---|
| 2 | 104 | 124 | 3.0 | 19 |
| 3 | 106 | 128 | 3.0 | 45 |
| 4 | 108 | 128 | 3.0 | 45 |
| 5 | 109 | 129 | 3.0 | 43 |
| 6 | 111 | 135 | 3.0 | 98 |
| 7 | 114 | 135 | 3.0 | 100 |
| 8 | 122 | 165 | 3.0 | 212 |
| 9 | 133 | 178 | 3.0 | 44 |
| 10 | 176 | 199 | 3.0 | 29 |
| 11 | 180 | 204 | 3.0 | 45 |
| 12 | 182 | 216 | 3.0 | 96 |
| 13 | 180 | 225 | 3.0 | 23 |

Fractions 4–10 are then bulked for redistillation. The resulting bulked fractions are redistilled on a 1' silver mirror column yielding the following fractions:

| FRACTION NO | VAPOR TEMP. (°C.) | LIQUID TEMP. (°C.) | VACUUM mm/Hg |
|---|---|---|---|
| 1 | 114/115 | 129/130 | 6.0/6.0 |
| 2 | 115 | 128 | 5.0 |
| 3 | 114 | 128 | 4.8 |
| 4 | 114 | 128 | 4.8 |
| 5 | 114 | 128 | 4.8 |
| 6 | 121 | 130 | 4.8 |
| 7 | 123 | 130 | 4.8 |
| 8 | 125 | 132 | 4.8 |
| 9 | 127 | 137 | 4.8 |
| 10 | 128 | 139 | 4.8 |
| 11 | 129 | 144 | 4.8 |
| 12 | 130 | 160 | 4.8 |
| 13 | 130 | 175 | 4.8 |

Fractions 4 to 11 of the second distillation are bulked for utilization in the following examples. Fractions 4–11 have a fruity, green, herbaceous, stemmy and floral aroma with green, anise-like, stemmy, oniony and parsley-like topnotes.

The resulting bulked fractions 4–11 contain compounds having the following structures:

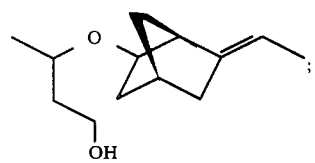

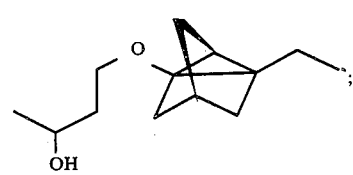

-continued

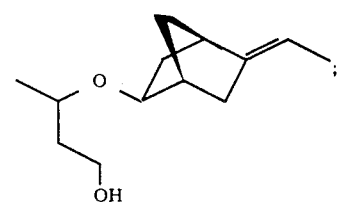

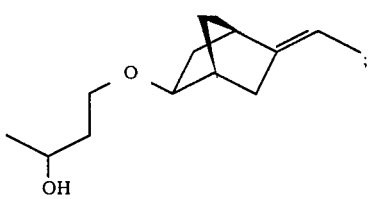

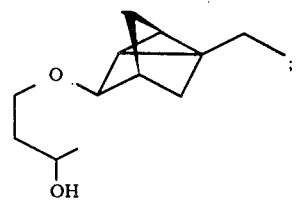

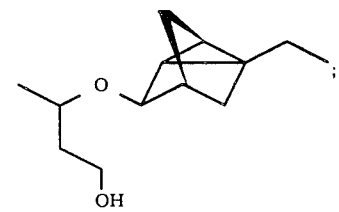

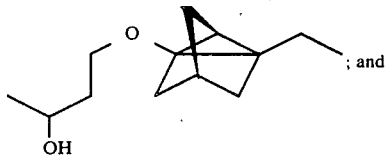; and

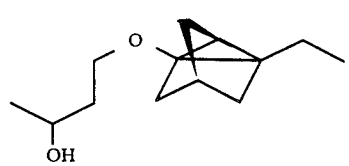

FIG. 1 is the GLC profile of the crude reaction product prior to any distillation (Conditions: 6'×0.25"10% SE-30 programmed at 180° C., isothermal).

FIG. 2 is the GLC profile for the bulked fractions 4–10 of the first distillation.

The peak indicated by Reference Numeral 21 is the peak for the mixture of compounds having the structures:

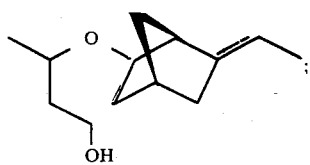
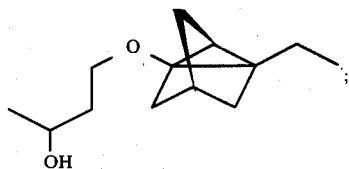
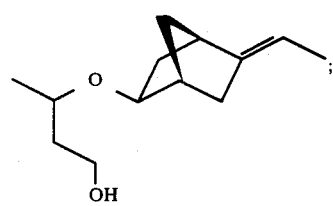
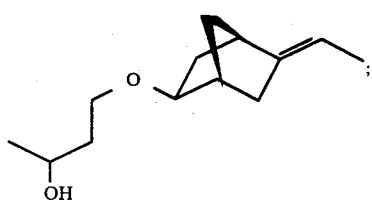
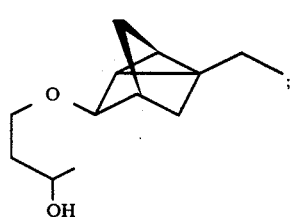
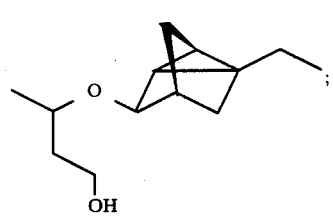
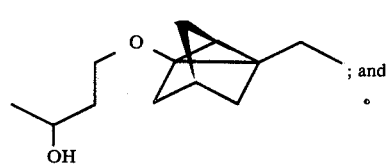
; and
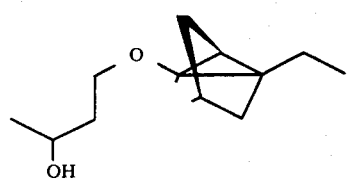
(GLC conditions: 6'×0.25"10% SE-30 column programmed at 200° C., isothermal).
FIG. 3 is the GLC profile for bulked fractions 4-11 of the second distillation (Conditions: 6'×0.25"10% SE-30 column programmed at 200° C., isothermal).
FIG. 4 is the NMR spectrum for the peak indicated by Reference Numeral 21 on FIG. 2 containing the compounds having the structures:
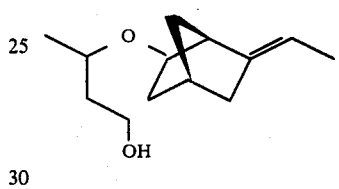
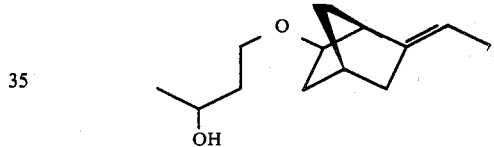
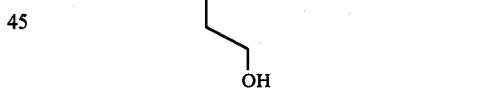
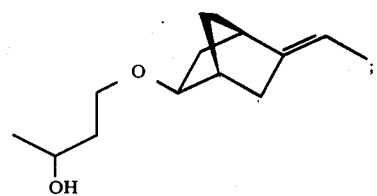
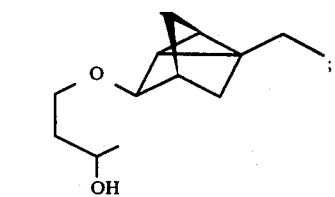

-continued
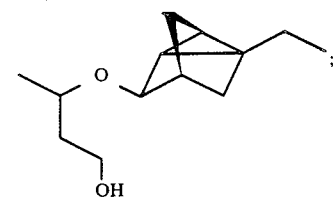
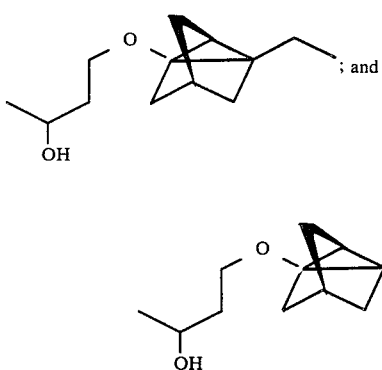
(Conditions: Field strength: 100 MHz; solvent: CFCl₃).
FIG. 5 is the infra-red spectrum for the peak indicated by Reference Numeral 21 on FIG. 2 containing the compounds having the structures:
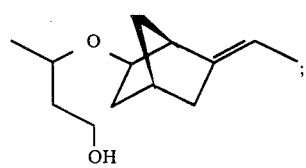
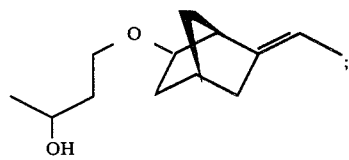
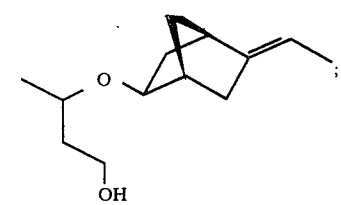
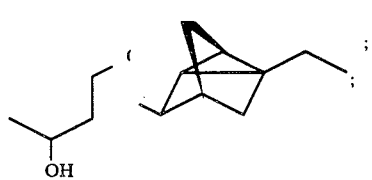
-continued
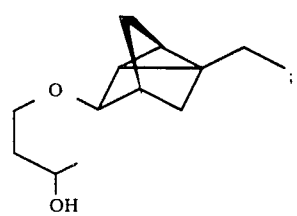
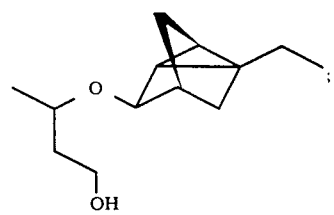
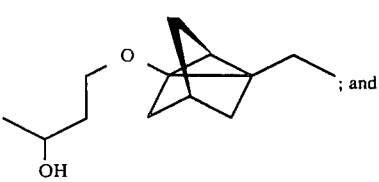
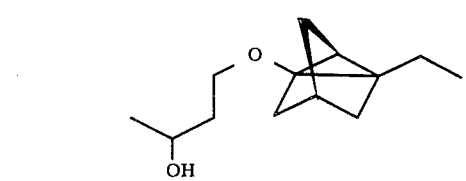
The mixture of compounds having the structures:
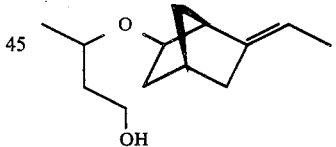
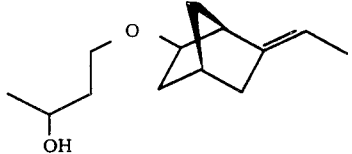
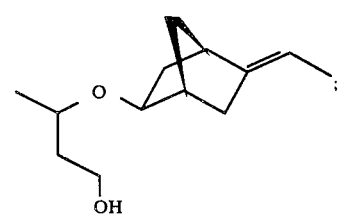

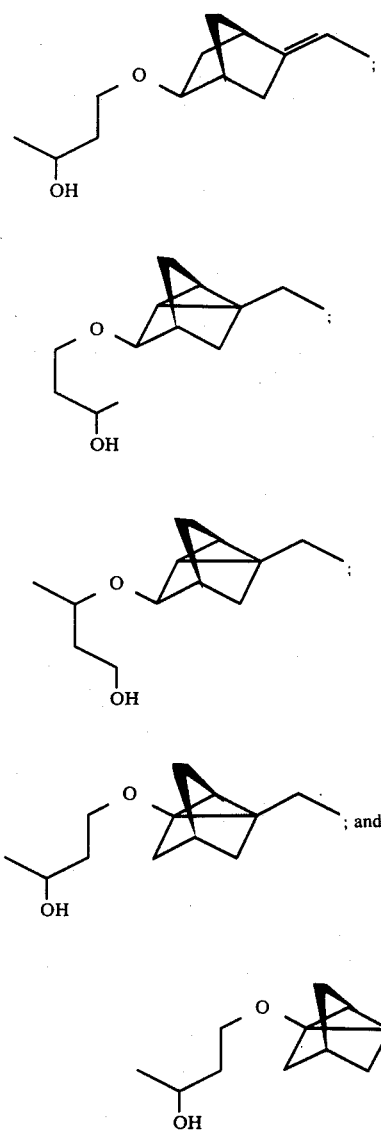

prepared according to Example I, bulked fractions 4–11, imparts a warm aesthetically pleasing, fruity, green, herbaceous and floral aroma with anise-like, alliaceous and parsley-like top-notes to this "floral/-woody cologne" composition.

Accordingly, the composition can be described as "floral, and woody with fruity, green, herbaceous undertones and faint anise-like, alliaceous and parsley-like topnotes".

EXAMPLE III

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| SUBSTANCE | AROMA DESCRIPTION |
|---|---|
| Mixture of compounds defined according to the structure: <br> ![structure] <br> wherein one of $R_1$ or $R_2$ is methyl and the other of $R_1$ or $R_2$ is hydrogen and wherein one of the dashed lines represents a carbon-carbon bond and the other of the dashed lines represents no bond, bulked fractions 4–11 produced according to Example I (second distillation) | A fruity, green, herbaceous and floral aroma with anise-like, alliaceous and parsley-like topnotes. |
| Perfume composition of Example II | A floral and woody aroma with fruity, green, herbaceous undertones and faint anise-like, alliaceous and parsley-like topnotes. |

EXAMPLE IV

PERFUMED LIQUID DETERGENT

Concentrated liquid detergents with aromas as set forth in Table I of Example III (which detergents are prepared from Lysine salt of n-dodecyl benzene sulfonic acid as more specifically described in United States Letters Patent, Ser. No. 3,948,818 issued on Apr. 6, 1976, the specification for which is incorporated by reference herein) are prepared containing each of the substances set forth in Table I of Example III, supra. They are prepared by adding and homogeneously mixing the appropriate quantity of perfumery substance as set forth in Table I of Example III in the liquid detergent. The detergents all possess aromas as set forth in Table I of Example, the intensity increasing with greater concentrations of perfumery substance of Table I of Example III, supra.

EXAMPLE V

PREPARATION OF A COLOGNE AND HANDKERCHIEF PERFUME

The perfume substances of Table I of Example III, supra, are incorporated into colognes at concentrations of 1.5%, 2.0%, 2.5%, 3.0% and 4.0% in 80%, 85%, and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table I of Example III are imparted to the cologne and to the handkerchief perfume compositions.

EXAMPLE VI

PREPARATION OF A DETERGENT COMPOSITION

A total of 100 grams of a detergent powder (a non-ionic detergent powder containing a proteolytic enzyme prepared according to Example I of Canadian Letters Patent No. 985,190 issued on Mar. 9, 1976, the disclosure of which is incorporated by reference herein) is mixed with 0.15 grams of each of the substances set forth in Table I of Example III, supra, until substantially homogeneous compositions are obtained. These compositions have excellent aromas as set forth in Table I of Example III.

EXAMPLE VII

PREPARATION OF SOAP

Each of the perfumery substances of Table I of Example III are incorporated into soap (LVU-1) at 0.1% by weight of each substance. After two weeks in the oven at 90° F., each of the soaps showed no visual effect from the heat. Each of the soaps manifested an excellent aroma as set forth in Table I of Example III, supra.

EXAMPLE VIII

PREPARATION OF SOAP COMPOSITION

One hundred grams of soap chips (IVORY ®, registered trademark of the Procter & Gamble Co. of Cincinnati, Ohio) are mixed individually with one gram each of the perfumery substances of Table I of Example III, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example III, supra.

EXAMPLE IX

PREPARATION OF A SOLID DETERGENT COMPOSITION

A detergent is prepared from the following ingredients according to Example I of Canadian Letters Patent No. 1,007,948, the specification for which is incorporated by reference herein:

| Ingredients | Parts by Weight |
| --- | --- |
| "Neodol 45-II" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table I of Example supra. The detergent samples each have excellent aromas as set forth in Table I of Example III, supra.

EXAMPLE X

Utilizing the procedure of Example 1 at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:
1. a water "dissolvable" paper ("Dissolvo Paper")
2. Adogen 448 (m.p. about 140° F.) as the substrate coating; and
3. an outer coating having the following formulation (m.p. about 150° F.);
    57 percent $C_{20-22}$HAPS
    22 percent isopropyl alcohol
    20 percent antistatic agent
    1 percent of one of the perfume substances of Table I of Example III, supra.

A fabric softening composition prepared as set forth above having the above aroma characteristics as set forth in Table I of Example III, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example III is imparted in a pleasant manner to the headspace in the dryer on operation thereof, using said dryer-added fabric softening non-woven fabric.

What is claimed is:
1. A process for augmenting or enhancing the aroma of a consumable material selected from the group consisting of perfume compositions, colognes and perfumed articles comprising the step of intimately admixing with said consumable material, an aroma augmenting or enhancing quantity of a mixture of compounds having the structures:

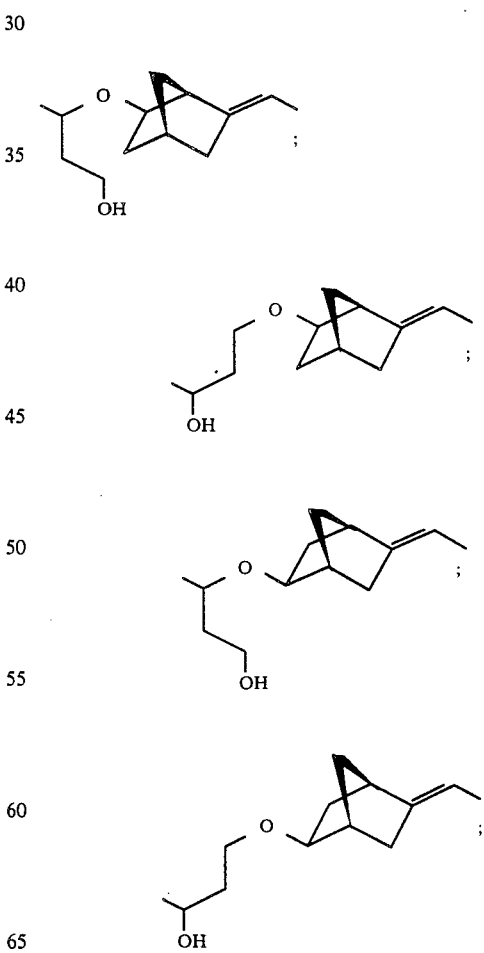

and

-continued

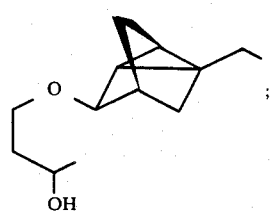
;

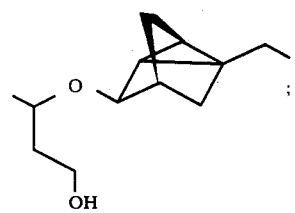
;

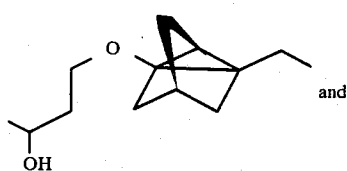
and

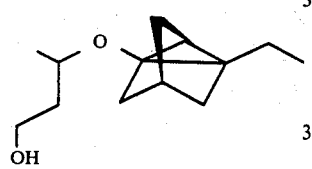

produced according to the process of reacting ethylidene norbornene having the structure:

with 1,3-dihydroxy butane having the structure:

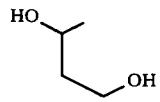

in the presence of a mineral acid catalyst or a Lewis acid catalyst at a temperature in the range of from about 25° C. up to about 120° C., the mole ratio of acid catalyst to ethylidene norbornene varying from about 1:99 up about 1:10; the mole ratio of ethylidene norbornene:1,3-butanediol varying from about 1:1 up to about 1:2 and then recovering said mixture by means of fractional distillation.

2. The process of claim 1 wherein the consumable material is a perfume composition, cologne or perfumed polymer.

3. The process of claim 1 wherein the consumable material is a perfumed article and the perfumed article is a solid or liquid anionic, cationic, nonionic or zwitterionic detergent.

4. The process of claim 1 wherein the consumable material is a perfumed article and the perfumed article is a fabric softener composition or a fabric softener article.

5. The process of claim 1 wherein the consumable material is a perfumed article and the perfumed article is a cosmetic powder.

* * * * *